United States Patent [19]

Sabins et al.

[11] Patent Number: 4,653,313

[45] Date of Patent: Mar. 31, 1987

[54] POSITIVE STIRRING CONSISTOMETER CUP AND METHOD OF USING THE SAME

[75] Inventors: Fred L. Sabins; David L. Sutton; Johnny W. Johnson, all of Duncan, Okla.

[73] Assignee: Halliburton Company, Duncan, Okla.

[21] Appl. No.: 788,992

[22] Filed: Oct. 18, 1985

[51] Int. Cl.[4] ............................................. G01N 11/14
[52] U.S. Cl. ........................................... 73/61.4; 73/60
[58] Field of Search ..................... 73/61.4, 59, 54, 60; 366/303, 253, 343

[56] References Cited

U.S. PATENT DOCUMENTS

| | | | |
|---|---|---|---|
| 338,136 | 3/1886 | Brush | 366/253 |
| 1,019,953 | 3/1912 | Fay | 366/253 X |
| 2,096,222 | 10/1937 | Bock | 265/11 |
| 2,122,765 | 7/1938 | Weiler | 265/11 |
| 2,266,733 | 12/1941 | Bays et al. | 265/11 |
| 2,273,750 | 2/1942 | Clagett, Jr. | 265/11 |
| 2,409,014 | 10/1946 | Bohmer et al. | 73/54 |
| 2,435,416 | 2/1948 | Thomson et al. | 18/8 |
| 2,603,087 | 7/1952 | Von Hortenau | 73/59 |
| 2,626,786 | 1/1953 | McGlothlin | 259/8 |
| 2,630,706 | 3/1953 | Maxon | 73/54 |
| 2,683,984 | 7/1954 | Boyle et al. | 73/59 |
| 2,821,079 | 1/1958 | Kerridge | 73/54 |
| 2,904,401 | 9/1959 | Booth | 23/188 |
| 3,027,756 | 4/1962 | Head | 73/53 |
| 3,269,171 | 8/1966 | Bruss et al. | 73/60 |
| 3,285,057 | 11/1966 | De Zurik | 73/59 |
| 3,347,089 | 10/1967 | Perry | 73/59 |
| 3,402,729 | 9/1968 | Richmond et al. | 137/92 |
| 3,407,618 | 10/1968 | Mullins, Jr. | 62/136 |
| 3,636,753 | 1/1972 | Thiele et al. | 73/59 |
| 3,709,664 | 1/1973 | Krekeler et al. | 366/303 X |
| 3,751,975 | 8/1973 | Katsura | 73/59 |
| 3,803,903 | 4/1974 | Lin | 73/59 |
| 3,875,791 | 4/1975 | Fitzgerald et al. | 73/59 |
| 4,044,602 | 8/1977 | Higgs et al. | 73/59 |
| 4,157,036 | 6/1979 | Kivenson | 73/290 |
| 4,175,425 | 11/1979 | Brookfield | 73/59 |
| 4,181,023 | 1/1980 | Clamroth et al. | 73/432 |
| 4,283,938 | 8/1981 | Epper et al. | 73/59 |
| 4,299,118 | 11/1981 | Gau et al. | 73/59 |
| 4,466,276 | 8/1984 | Ruyak et al. | 73/59 |
| 4,484,468 | 11/1984 | Gau et al. | 73/60 |

FOREIGN PATENT DOCUMENTS 972327 11/1982 U.S.S.R. ................................... 73/59

OTHER PUBLICATIONS

SPE 9285 "Transition Time of Cement Slurries Between the Fluid and Set State", p. 3897, vol. 41, Halliburton Services Sales and Service Catalog.

"Description of Stirring Chamber," Halliburton Services.

"Oil Well Cement Testing Equipment—Atmospheric Pressure Consistometer, Chandler Engineering Company.

NOWSCO News—Compact Pressurized Consistometer, NOWSCO Well Service, Ltd.

Primary Examiner—Michael J. Tokar
Assistant Examiner—Joseph W. Roskos
Attorney, Agent, or Firm—James R. Duzan; E. Harrison Gilbert, III

[57] ABSTRACT

A positive stirring consistometer cup includes a pair of wall blade members having radially inwardly extending blades which cooperate with radially outwardly extending blades of a paddle to uniformly apply shear throughout a substance to be tested. A split sleeve assembly eliminates an outer dead space, and an enlarged spacer member mounted on the shaft of the paddle eliminates an inner dead space, thereby enhancing the uniformity of the shear throughout the substance. A centralizing assembly centers the stationary paddle while causing a minimum of friction and wear to occur on the shaft of the paddle. In a method of using the positive stirring consistometer cup, the blades of the wall blade members and of the paddle stop in substantially aligned, coplanar relationship to facilitate cleaning of the elements after a test is concluded.

17 Claims, 2 Drawing Figures

POSITIVE STIRRING CONSISTOMETER CUP AND METHOD OF USING THE SAME

BACKGROUND OF THE INVENTION

This invention relates generally to consistometer container assemblies and methods of using them with a substance to be tested therein and more particularly, but not by way of limitation, to a positive stirring consistometer container assembly (hereinafter referred to as a "cup") and method of handling a thixotropic substance which is initially flowable but subsequently hardens into a solid attached to parts of the cup.

In the oil and gas industry, different fluids are used for various purposes in drilling and completing as well. For example, batches of cement slurry must be mixed and pumped into the well for cementing the casing into the well bore. The cement is generally pumped through the casing and up the annulus between the well casing and the well bore to create the necessary bond.

Because different batches of fluids (e.g., cement slurriers) can have different characteristics which affect how the fluids perform in the high temperature and high pressure environments found downhole, there is the need for equipment which can test a fluid sample prior to the fluid being pumped downhole so that one can determine if that particular batch of fluid has the proper characteristics for the particular situation. Such a type of equipment is known to the art, as exemplified by a high temperature-high pressure consistometer provided by Halliburton Services or one provided by Chandler Engineering.

Prior to the commencement of an actual cement job, for example, a particular type of slurry composition proposed to be used on the job is thoroughly tested in a cement testing laboratory, such as one where the aforementioned Halliburton Services or Chandler Engineering consistometer is used. One of the major areas of testing concerns the fluid life and pumpability of the cement slurry. The ultimate objective to be achieved by the test is to insure that the cement slurry to be used can be placed with reasonable time safety. At least one property indicating whether the particular cement slurry will achieve this objective can be obtained through a thickening time test performed via the consistometer.

Although the purpose of such a thickening time test is to simulate the pumping of the cement slurry in the downhole environment to test at least one of the characteristics of the slurry (particularly, the total fluid time of the slurry), the thickening time test which has been performed with at least one type of prior art consistometer cup provides only a relatively small amount of shear to the entire volume of the slurry tested. This prior art cup includes a container for holding the cement slurry and a paddle disposed in the container and relative to which the container rotates. The cement slurry at the interface of this container experiences shear, but the cement slurry near the center of the container experiences very little shear. This phenomenon can contribute to the shortcomings of such a prior art cup whereby reliable and repeatable results are difficult to obtain. It is also difficult to adequately test special or problem blends, such as thixotropic compositions. These shortcomings can result in seemingly inconsistent data obtained from identical tests performed on similarly constituted pilot and field blends, which can result in extensive and expensive expenditures of laboratory time and manpower.

One example of these shortcomings is manifested in the testing of thixotropic substances, such as a cement slurry having a rapidly increasing apparent viscoisty at decreasing shear rate and having a high rate of static gel strength increase imparted by adding thixotropic cross-linked materials or as a by-product of gas generating additives or as a result of a high concentration of water absorbing materials. Such thixotropic substances are even more sensitive to shear than conventional cement slurries, for example. Because of this, a reliable measurement of conventional thickening time is hard to obtain when only a small amount of shear is imparted to the thixotropic substance. Such thickening times obtained by using prior art cups have been found to indicate a shorter thickening time or a high degree of premature gelling when such indications are not in fact accurate descriptions of the particular substance tested. This has resulted in such blends being chemically modified to have their thickening times retarded and thier viscosities lowered when in actuality such additions or modifications were not needed, as would have been indicated if a more reliable thickening time had been measured. These modifications, by which the blend is over-retarded and over-dispersed, can result in delayed compressive strength development once the actual field blend is pumped into the well bore so that it takes longer for the cement to properly bond. This increases the "waiting on cement" time and, correspondingly, the cost; it also decreases the thixotropic properties for which the slurry was formulated.

As another example of the shortcomings of such prior art consistometer cups, it has been found that repeatable test results between seemingly identical tests on identical slurries under high pressure applications have a great deal of variation.

From the foregoing, it is apparent that there is the need for an improved consistometer cup which can be used with existing test apparatus to more reliably and repeatedly obtain thickening time measurements of substances, such as conventional and special cement blends. A concomitant method of using such a cup to more easily handle the test substance is also needed.

SUMMARY OF THE INVENTION

The present invention overcomes the above-noted and other shortcomings of the prior art by providing a novel and improved consistometer container assembly, or cup, and method of using the same. By the present invention, a uniform shear is applied to the entire substance tested whereby more reliable and repeatable measurements are obtained. The preferred embodiment of the present invention particularly provides a way to better measure the thickening time of special compositions, such as thixotropic and problem slurries.

The novel aspects of the present invention include a pair of wall blade members which rotate with a container of the cup so that the substance to be tested will undergo positive stirring which will apply shear uniformly throughout the test substance. A pair of split sleeve members act as a spacer along the inside of the container fitted up to the wall blade members to provide a uniform smooth cylinder for the stirring assembly. This eliminates or reduces outer dead flow areas and eases the clean-up of the cup once the substance is set. An enlarged-center paddle shaft is used to minimize the low shear rate dead space in the center of the container, thereby preventing or reducing premature crystal growth so that the cement slurry does not prematurely viscosify or thicken.

More particularly, the positive stirring consistometer cup of the present invention comprises a container having an interior surface bounding a hollow region defined in the container; a wall blade member having a support web and a plurality of spaced first protuberances extending from the web, the member removably disposed in the container so that a surface of the web lies adjacent the interior surface of the container; a split sleeve assembly removably retained within the container adjacent the interior surface, the split sleeve assembly having two end surfaces engaging opposite sides of the web; a paddle having a plurality of spaced second protuberances extending therefrom so that the second protuberances pass through the spaces between the first protuberances of the wall blade member when the wall blade member rotates relative to the paddle; and retainer means for releasably retaining the paddle, the wall blade member and the split sleeve assembly in the container. The paddle includes spacer means, connected to a shaft so that the spacer means occupies a central volume of the hollow region of the container, for preventing premature crystal growth within a substance received in the container for testing, which spacer means has the second protuberances extending therefrom. The retainer means more particularly includes centralizing means for maintaining the shaft of the paddle centrally disposed within the hollow region of the container, and it includes a retaining ring and retaining baffle cooperating with the wall blade member and split sleeve assembly.

In the preferred embodiment, the cup further comprises another wall blade member disposed in the container in cooperating relationship with the first-mentioned wall blade member and the paddle so that a shear force is applied, during relative rotation between the paddle and the wall blade members, substantially uniformly across the substance received in the hollow region of the container. The split sleeve assembly particularly includes a pair of sleeve members disposed circumferentially around the interior of the container on opposite sides of the wall blade members.

The method of the present invention as specifically used in the handling of a substance which hardens in a consistometer comprises assembling a positive stirring consistometer cup so that blades of a paddle therein interact with a pair of wall blade members therein to apply shear across the substance; flowing the substance into the assembled cup; testing the substance, including rotating the wall blade members relative to the paddle; stopping the relative rotation of the wall blade members and the paddle so that the wall blade members and the paddle are substantially aligned in response to at least a portion of the substance hardening; withdrawing the hardened substance from the cup simultaneously with the substantially aligned wall blade members and paddle; and removing the hardened substance from the substantially aligned wall blade members and paddle.

From the foregoing it is a general object of the present invention to provide a novel and improved consistometer cup and method of using the same. Other and further objects, features and advantages of the present invention will be readily apparent to those skilled in the art when the following description of the preferred embodiment is read in conjunction with the accompanying drawings.

DETAILED DESCRIPTION OF THE PREFERRED EMBODIMENT

Figure 1:
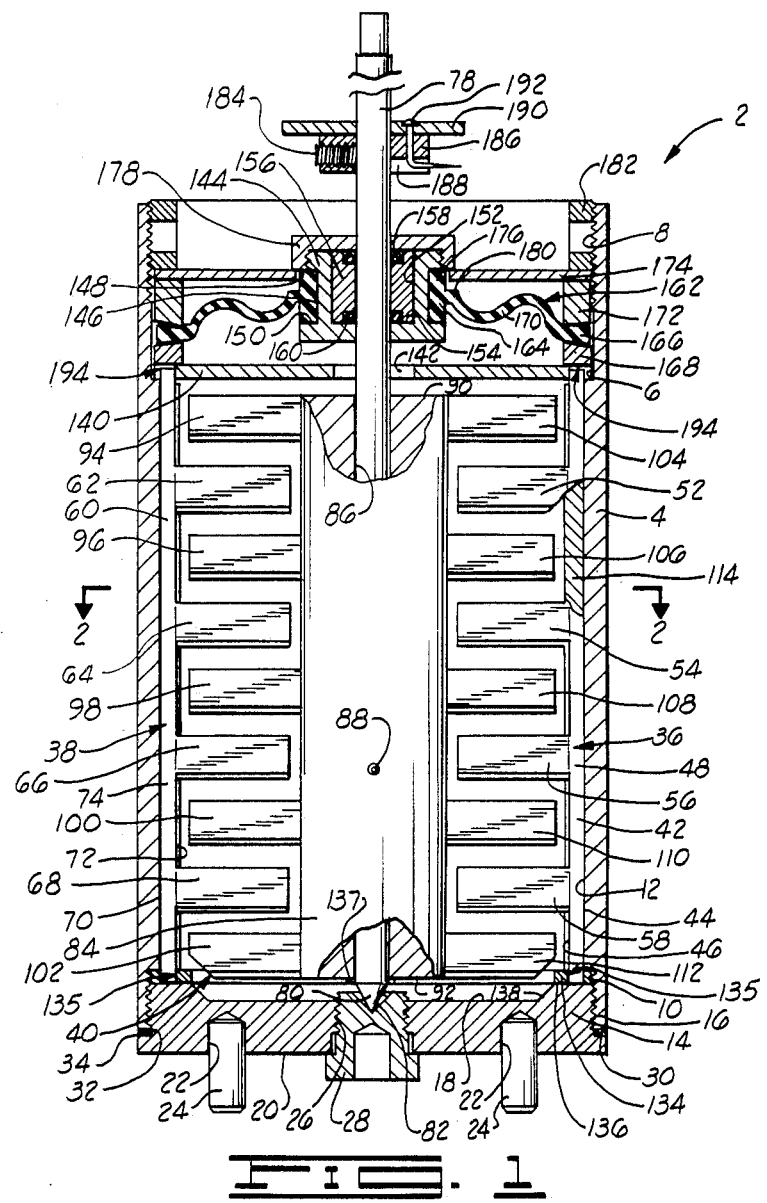
FIG. 1 is a partially sectional elevational view of the preferred embodiment of the consistometer cup of the present invention.
Figure 2:
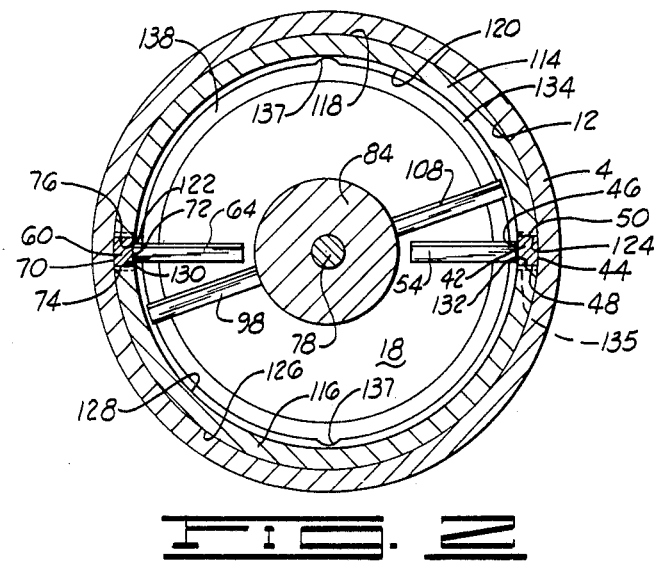
FIG. 2 is a sectional plan view taken along line 2—2 shown in FIG. 1.

With reference to FIGS. 1 and 2, a positive stirring consistometer cup 2 constructed in accordance with the preferred embodiment of the present invention will be described. The cup 2 broadly includes a container, stirring means for applying a shear force to a substance received in the container, a split sleeve assembly, and retainer means for releasably retaining the stirring means and the split sleeve assembly in the container.

The container includes a cylindrical sleeve element 4 having an upper recessed surface 6, including a threaded portion 8, and having a lower recessed surface 10 which is threaded. Extending axially between the recessed surfaces 6, 10 is a cylindrical interior surface 12 defining part of a hollow interior region of the container.

The container also includes a base element 14 having a recessed circumferential surface 16 which is threaded for engaging with the threaded recessed surface 10 of the sleeve element 4. The base element 14 has an inner surface 18 defining a bottom of the hollow region within the container. An outer surface 20 of the base element 14 has a plurality of indentations 22 formed therein for receiving roll pins 24 which are engageable by a rotating mechanism to rotate the container in a manner as known to the art. The base element 14 also has a central opening 26 defined therethrough for receiving a suitable plug 28, which opening 26 provides a vent port which is used when filling the container with the test slurry or fluid.

The container also includes a base gasket 30 shown in FIG. 1 disposed between an upwardly facing annular shoulder surface 32 of the base element 14 and a downwardly facing annular end surface 34 of the sleeve element 4.

Disposed within the container is the stirring means which includes two wall blade members 36, 38 and a paddle 40.

The wall blade member 36 includes a vertically extending linear support web 42 having an outer circumferential surface 44, an inner circumferential surface 46, and opposite radial surfaces 48, 50. Extending vertically inwardly from the same side of the support web 42 (specifically from the inner circumferential surface 46) are a plurality of spaced protuberances specifically embodies as four angular blades 52, 54, 56, 58. The blades 52, 54, 56, 58 are vertically aligned for the disposition of the wall blade member 36 shown in FIG. 1. In this disposition, the surface 44 of the wall blade member 36 lies adjacent the surface 12 of the sleeve element 4.

The wall blade member 38 is constructed similarly to the wall blade member 36. In particular, it includes a linear support web 60 from which blades 62, 64, 66, 68 radially protrude. The web 60 has an outer circumferential surface 70, an inner circumferential surface 72 and opposing radial surfaces 74, 76. The wall blade member 38 is disposed in the container so that the surface 70 lies adjacent the interior surface 12 of the container. In the preferred embodiment, the wall blade member 38 is disposed in cooperating relationship with the wall blade member 36 so that a shear force is applied substantially uniformly across the substance in the container when there is relative motion between the wall blade members 36, 38 and the paddle 40. More particularly, the wall blade member 38 is disposed so that each of the blade protuberances 62, 64, 66, 68 is diametrically aligned with a respective one of the blade protuberances 52, 54, 56, 58 as shown in FIGS. 1 and 2. In this disposition, the wall blade members 36, 38 are coplanarly related by including a plane extending axially through the cup 2 and including a diameter thereof.

The wall blade members 36, 38 are releasably retained within the container by portions of the aforementioned retainer means as will be more particularly described hereinbelow. At present, however, it is to be noted that the wall blade members 36, 38 are suitably retained so that when they are fully disposed within the container, they are fixed relative thereto so that they rotate when the container is rotated through the rotative coupling action provided by the roll pins 24.

Interacting with the wall blade members 36, 38 to produce the uniform shear is the paddle 40 which includes a longitudinal shaft 78 having a lower end 80 rotatably received within a depression defined by a surface 82 of the plug 28. The paddle 40 also includes a cylindrical spacer member 84 having an axial bore 86 defined therethrough for receiving the shaft 78. The shaft 78 and the member 84 are connected to each other in fixed relationship by a pin 88 to prevent relative rotation therebetween. The member 84 is connected to the shaft 78 so that the member 84 extends axially between an annular upper surface 90 and an annular lower surface 92 which is disposed near and facing the surface 18 of the base element 14.

The spacer member 84 occupies a central volume of the hollow region of the container when the paddle 40 is disposed therein, whereby a central dead zone found in other consistometer cups is eliminated or reduced. This provides means for preventing premature crystal growth within a thixotropic substance, for example, under test. This prevents or reduces gelling and the consequent cake build-up which would otherwise accumulate on the paddle, thereby enhancing the shear application throughout the entire volume of the test substance.

Extending radially outwardly from the member 84 is a plurality of protuberant blades 94, 96, 98, 100, 102, 104, 106, 108, 110, 112. The blades 94, 96, 98, 100, 102 define a vertically arrayed set of spaced protuberances extending from a common longitudinal portion of the member 84, and the blades 104, 106, 108, 110, 112 define another set of vertically aligned protuberances extending from another common longitudinal portion of the member 84. In the preferred embodiment the two sets are disposed on diametrically opposite portions of the member 84. This construction places these protuberances of the paddle 40 in a coplanar relationship with each other. Each blade of a set is spaced vertically from each other blade within the set and extends from a respective portion of the member 84 so that as the container rotates, thereby simultaneously rotating the wall blade members 36, 38, the blades of the wall blade members 36, 38 and the blades of the paddle 40 pass through the respective spaces of the other each one-half revolution. With this construction wherein the wall blade members 36, 38 are coplanarly related and the sets of protuberances of the paddle 40 are coplanarly related, the present invention operates with a thixotropic substance, for example, or any other suitable substance which hardens, whereby as the substance hardens, the relative rotation stops with all the protuberances substantially coplanar aligned. Thus, the test substance, or at least a portion thereof, hardens into a solid form having substantially two readily removable portions on opposite sides of the substantially coplanarly related protuberances. This enhances the ease by which the hardened substance can be knocked or otherwise removed from the wall blade members 36, 38 and the paddle 40.

The split sleeve assembly of the cup 2 is removably retained within the container adjacent the interior surface 12. In the preferred embodiment the split sleeve assembly includes two semicylindrical sleeve members 114, 116. The sleeve members 114, 116 are disposed circumferentially around the interior of the container on opposite sides of the wall blade members 36, 38 as best shown in FIG. 2.

The sleeve member 114 has an outer circumferential surface 118 disposed adjacent the interior surface 12 of the container. The sleeve member 114 has an inner circumferential surface 120. The sleeve member 114 terminates in longitudinal end surfaces 122, 124 which are disposed adjacent and engage the surface 76 of the wall blade member 38 and the surface 50 of the wall blade member 36, respectively.

The sleeve member 116 has an outer circumferential surface 126 disposed adjacent the interior surface 12 of the container. The sleeve member 116 has an inner circumferential surface 128 and longitudinal end surfaces 130, 132. The surface 130 engages the surface 74 of the wall blade member 38, and the surface 132 engages the surface 48 of the wall blade member 36.

The combination of the split sleeve members 114, 116 defines a removable wall means for preventing the formation of dead space adjacent the interior surface of the container and near the extremities of the blades of the paddle 40. This enhances the application of the shear forces throughout the entire volume of the test substance when there is relative rotational movement between the blades of the paddle 40 and the blades of the wall blade members 36, 38.

The split sleeve members 114, 116 are made of a suitable material, such as plastic or stainless steel. The other parts of the cup 2 are likewise made of suitable materials known to the art.

The retainer means includes a retaining ring 134 disposed in the bottom of the container adjacent an annular surface 136 of the base element 14 spaced above the surface 18 thereof by a beveled surface 138 as shown in FIG. 1. The retaining ring 134 is also disposed adjacent a lower circumference of the wall blade members 36, 38 and the sleeve members 114, 116. The retaining ring 134 includes two diametrically opposite, outwardly facing slots 135 acting to hold the lower ends of the wall blade members 36, 38 against the interior surface 12 of the container. The retaining ring 134 also includes two diametrically opposite, inwardly facing half-moon notches 136 that are disposed in the ring perpendicularly to the line on which the slots 135 are disposed. The notches 137 allow the ends of the paddle blades 94–112 to pass therethrough so that the paddle 40 can be installed after the retaining ring 134 has been installed, as more particularly described hereinbelow. When the ring 134 is installed in the container, its upper surface supports or engages the lower edges of the sleeve members 114, 116.

Holding the upper portions of the wall blade members 36, 38 against the surface 12 of the container is a retaining baffle plate 140 having slots defined therein receiving the top ends of the wall blade members 36, 38. The retaining baffle 140 has a central opening 142 defined therein through which the shaft 78 extends. The retaining baffle 140 is disposed at a height in the container so that the surface 90 of the spacer member 84 is disposed near thereto and so that the upper edges of the sleeve members 114, 116 are adjacent thereto. The retaining baffle 140 and the retaining ring 134 define in the preferred embodiment means for releasably securing the wall blade members 36, 38 and the sleeve members 114, 116 in relative fixed positions within the container.

Mounted on top of the retaining baffle 140 is a centralizing means for maintaining the shaft 78 of the paddle 40 centrally disposed within the hollow region of the container. The centralizing means forms another part of the retainer means.

The centralizing means of the preferred embodiment includes a cylindrical hub 144 having a circumferential groove defined therein by surfaces 146, 148, 150. An upwardly open cavity or hollow interior is defined within the hub 144 by a cylindrical surface 152 and an annular surface 154 extending radially inwardly from a lower edge of the surface 152. The hub 144 is disposed above the retaining baffle 140 with the shaft 78 extending centrally therethrough.

Disposed within the interior region defined by the surfaces 152, 154 are a packing or spacer plug or bushing 156 and O-rings 158, 160. The bushing 156 and the O-rings 158, 160 surround the respective portion of the shaft 78 in a manner which tends to minimize the frictional engagement therewith and wear thereon.

Extending radially outwardly from the circumferential groove of the hub 144 is a rubber diaphragm 162 having an inner annular portion 164 received in the circumferential groove 144 and having an outer portion 166 disposed on top of an annular diaphragm collar 168 which is mounted on top of the outer periphery of the retaining baffle plate 140. Intermediate the portions 164, 166 of the diaphragm 162 is an undulating portion 170.

This assembly including the hub 144, the bushing 156 and the diaphragm 162 is mounted to secure and positively align the paddle 40 centrally within the container. This mounting is by means of the aforementioned diaphragm collar 168 forming a part of the centralizing means. This mounting is also achieved by a top baffle spacer ring 172 disposed on top of the outer portion 166 of the diaphragm 162. Also implementing this mounting technique is a top baffle plate 174 having its outer periphery supported on the top baffle spacer ring 172 and having a cylindrical inner surface 176, defining an opening through the center of the plate 174, disposed near the top of the annular portion 164 of the diaphragm 162 as shown in FIG. 1. To prevent the assembly from moving downwardly relative to the plate 174, the retainer means also includes a hub cap 178 threadedly connected to the top of the hub 144 in engagement with the inner periphery of the baffle plate 174. Upward movement of the assembly is limited by the spacing, if any, between the baffle plate 174 and an annular shoulder surface 180 of the diaphragm 162. Lateral movement is limited by any spacing between the surface 176 of the baffle plate 174 and the outer surface of the annular portion 164 of the diaphragm 162. This construction provides positive alignment of the shaft 78 to prevent or reduce lateral movement thereof.

Vertical movement of the shaft 78 is limited in the downward direction by the engagement of the shaft 78 with the surface 82 of the plug 28 and in the upward direction by the spacing between the surface 90 of the member 84 (and the upper surface of the top blades 94, 104) and the lower surface of the retaining baffle 140.

Completing the retainer means is a lock ring 182 which threadedly engages with the threaded surface 8 of the sleeve element 4 in downward engagement of the plate 174.

Connected by a set screw 184 to the shaft 78, above the lock ring 182, is a drive disc 186 having a notch 188 defined therein. The drive disc 186 is connected to a drive bar 190 by as pin 192 in a manner and for a purpose as known to the art, except that the lower end of the pin 192 is bent up into the notch 188 as shown in FIG. 1 so that the pin 192 does not engage the hub cap 178.

In operation, such as by being used to handle a thixotropic substance which is to have its thickening time measured, the present invention includes assembling the positive stirring consistometer cup 2 so that the blades of the paddle 40 suitably interact with the pair of wall blade members 36, 38 to apply shear uniformly across the thixotropic substance. Once the cup is assembled to a suitable degree, the substance is flowed into the container and the testing conducted. During such testing, the roll pins 24 are engaged to rotate the container, with the wall blade members 36, 38 and the sleeve members 114, 116 fixed thereto, relative to the paddle 40. During such rotation, the blades of the wall blade members 36, 38 pass through the spaces between the blades of the paddle 40 in interleaving relationship therewith. Such action increases the shear across the substance so that the average shear rate throughout the entire substance is increased over that which has been obtainable with the prior art cups not containing the wall blade members of the present invention. Such increase in shear aids in preventing premature gelling through premature crystal growth within the thixotropic substance being tested.

The operation of the present invention in handling the thixotropic or other suitable substance also includes stopping the relative rotation of the wall blade members 36, 38 and the paddle 40 so that the wall blade members and the paddle are substantially aligned in response to at least a portion of the substance hardening, such as by the setting of a suitable cement slurry embodying a specific type of thixotropic substance. This step of stopping the relative rotation with the wall blade members and the paddle in this substantially aligned position has been found to be an unexpected, inherent feature resulting from the novel construction of the cup of the present invention. This feature is a significant advantage of the present invention because it simplifies the removal of the hardened substance from the wall blade members 36, 38 and the paddle 40. That is, once the relative rotation has been stopped, the wall blade members 36, 38 and the paddle 40 can be simultaneously removed from the container and the hardened substance can be removed in substantially two halves. This is distinguishable over a situation wherein the blades of the paddle 40 would be in an offset relationship to the blades of the wall blade members 36, 38 so that four, rather than two, sectors would be defined. This can be envisioned by viewing FIG. 2 and mentally rotating the blades of the wall blade members 36, 38 relative to the blades of the paddle 40.

In specifically assembling the positive stirring consistometer cup shown in FIGS. 1 and 2, the top retaining elements are first releasably secured in the top of the container. This includes inserting the retaining baffle 140 into the sleeve element 4 to the position shown in FIG. 1. Following this in sequence are the inserting and positioning of the diaphragm collar 168, the hub-bushing-diaphragm assembly, the top baffle spacer ring 172, and the top baffle plate 174. The lock ring 182 and the hub cap 178 are then installed. With this assembly completed, the sleeve element 4 is turned over into an upside down position relative to its rightside up position shown in FIG. 1. The sleeve members 114, 116 and the wall blade members 36, 38 are slid through the open bottom of the sleeve member 4 into the interior region of the sleeve member 4 and properly positioned or moved relative to the retaining baffle 140 so that the top ends of the wall blade members 36, 38 are received for securing engagement in outwardly facing slots or notches 194 defined in the baffle 140 and so that the sleeve members 114, 116 are on opposite sides of the wall blade members 36, 38 whereby the wall blade members 36, 38 are disposed diametrically opposite each other. Next, the retaining ring 134 is inserted so that the outer slots 135 receive the lower ends of the wall blade members 36, 38. The paddle 40 is installed by inserting it through the open bottom of the container and moving it so that the paddle shaft 78 goes through the top retaining elements and the paddle blades enter through the inner slots 137 of the retaining ring 134 whereby the paddle blades do not become engaged with the wall blades during such assembling. Finally, the base gasket 30 and the base element 14 assembly are connected to the sleeve member 4 to close the bottom of the container.

To enhance the ease with which the removable members are separated from the container at the conclusion of a test, the step of assembling the preferred embodiment further includes applying grease over the surfaces of the sleeve members 114, 116, the wall blade members 36, 38, the paddle shaft 78 and the bushing 156.

From the foregoing, it is apparent that the present invention provides a uniform shear to the entire substance being tested. This uniformity is achieved through the use of the interleaved stationary and rotating blades and the elimination or reduction of dead spaces near the center (by means of the enlarged spacer member 84) and near the outer periphery of the blades of the paddle 40 (by means of the removable sleeves 114, 116). Such construction provides a better repeatability of tests and a better reliability of the measurement data, such as the thickening time of thixotropic substances. For example, the present invention applies enough shear so that a more accurate thickening time, rather than premature gelation, of a thixotropic slurry is measured. Thus the repeatability and reliability provided by the present invention are an improvement over the prior art. By the construction of the present invention, not only standard substances, but also thixotropic and other problem-type or special slurries for which adequate measurements have heretofore been difficult to obtain can be accurately tested.

Thus, the present invention is well adapted to carry out the objects and attain the ends and advantages mentioned above as well as those inherent therein. While a preferred embodiment of the invention has been described for the purpose of this disclosure, numerous changes in the construction and arrangement of parts and the performance of steps can be made by those skilled in the art, which changes are encompassed within the spirit of this invention as defined by the appended claims.

What is claimed is:

1. A positive stirring consistometer cup, comprising:
   a container having an interior surface bounding a hollow region defined in said container;
   a wall blade member having a support web and a plurality of spaced first protuberances extending from said web, said member removably disposed in said container so that a surface of said web lies adjacent said interior surface of said container;
   a split sleeve assembly removably retained within said container adjacent said interior surface, said split sleeve assembly having two end surfaces engaging opposite sides of said web;
   a paddle having a plurality of spaced second protuberances extending therefrom so that said second protuberances pass through the spaces between said first protuberances of said wall blade member when said wall blade member rotates relative to said paddle; and
   retainer means for releasably retaining said paddle, said wall blade member and said split sleeve assembly in said container.

2. A consistometer cup as defined in claim 1, wherein said paddle includes:
   a shaft rotatively received in said container; and
   spacer means, connected to said shaft so that said spacer means occupies a central volume of said hollow region of said container, for preventing premature crystal growth within a substance received in said container for testing, said spacer means having said second protuberances extending therefrom.

3. A consistometer cup as defined in claim 2, wherein said retainer means includes centralizing means for maintaining said shaft of said paddle centrally disposed within said hollow region of said container.

4. A consistometer cup as defined in claim 1, wherein said retainer means includes centralizing means for maintaining said paddle centrally disposed within said hollow region of said container.

5. A consistometer cup as defined in claim 1, wherein:
   said cup further comprises another wall blade member having a second support web and a plurality of spaced third protuberances extending from said second web, said another wall blade member removably disposed in said container with said second web adjacent said interior surface of said container diametrically opposite said first-mentioned wall blade member so that said two wall blade members are coplanarly related and so that each respective one of said third protuberances is diametrically aligned with a respective one of said first protuberances; and
   said second protuberances extend from said paddle in coplanar relationship so that when a substance received within the hollow interior of said container hardens as said paddle and said wall blade members rotate relative to each other, said rotation stops with said first, second and third protuberances substantially coplanarly aligned, whereby the hardened substance is formed in substantially two readily removably portions on opposite sides of the substantially coplanarly related protuberances.

6. A consistometer cup as defined in claim 5, wherein said split sleeve assembly includes a first semicylindrical sleeve member, having a first one of said two end surfaces and having a third end surface adjacent said second web, and a second semicylindrical sleeve member, having a second one of said two end surfaces and having a fourth end surface adjacent said second web, said first and second sleeve members defining a removable wall means for preventing the formation of a dead space adjacent said interior surface of said container when the substance is received therein and said wall blade members rotate relative to said paddle.

7. A consistometer cup as defined in claim 6, wherein said retainer means includes:
   a retaining ring disposed in the bottom of said hollow interior of said container adjacent a lower circumference of said wall blade members and said sleeve members; and
   a retaining baffle disposed in said container and having slots defined therein receiving top ends of said wall blade members.

8. A consistometer cup as defined in claim 7, wherein said paddle further includes a cylindrical spacer member, having an axial bore defined therethrough in which said shaft of said paddle is received and having said second protuberances extending therefrom, said spacer member connected to said shaft so that said spacer member extends substantially between a bottom of said container and said retaining baffle.

9. A consistometer cup as defined in claim 1, further comprising another wall blade member disposed in said container in cooperating relationship with said first mentioned wall blade member and said paddle so that a shear force is applied, during relative rotation between said paddle and said wall blade members, substantially uniformly across a substance received in said hollow region of said container.

10. A consistometer cup as defined in claim 9, wherein said split sleeve assembly includes a pair of sleeve members disposed circumferentially around the interior of said container on oposite sides of said wall blade members, one of said sleeve members having one of said two end surfaces and the other of said sleeve members having the other of said two end surfaces.

11. A positive stirring consistometer cup, comprising:
   a container;
   stirring means, disposed in said container, for applying a shear force to a substance received in said container, said stirring means including a paddle having a shaft and further including a pair of vertical wall blade members disposed in said container in cooperating relationship with said paddle so that a shear force is applied uniformly across the substance received in said container;
   retainer means for retaining said stirring means in said container; and
   a pair of sleeve members disposed circumferentially around the interior of said container on opposite sides of said wall blade members.

12. A consistometer cup as defined in claim 11, wherein said retainer means further includes means for releasably securing said wall blade members and said sleeve members in relative fixed position within said container.

13. A method of handling a substance which hardens in a consistometer, comprising:
   assembling a positive stirring consistometer cup so that blades of a paddle therein interact with a pair of wall blade members therein to apply shear across the substance;
   flowing the substance into the assembled cup;
   testing the substance, including rotating said wall blade members relative to said paddle;
   stopping the relative rotation of the wall blade members and the paddle so that the wall blade members and the paddle are substantially aligned in response to at least a portion of the substance hardening;
   withdrawing the hardened substance from the cup simultaneously with the substantially aligned wall blade members and paddle; and
   removing the hardened substance from the substantially aligned wall blade members and paddle.

14. A method as defined in claim 13, wherein the step of assembling includes:
   inserting the pair of wall blade members into a container;
   inserting a pair of sleeve members, forming the parts of a split sleeve assembly, into the container on opposite sides of the pair of wall blade members so that the wall blade members are disposed diametrically opposite each other;
   inserting the paddle into the container between the wall blade members; and
   releasably retaining the wall blade members, the sleeve members and the paddle in the container.

15. A method as defined in claim 14, wherein:
   the wall blade members, sleeve members and paddle are inserted through an open bottom of the container; and
   the step of releasably retaining includes:
      prior to the steps of inserting the wall blade members, the sleeve members and the paddle, releasably securing a retaining baffle and centralizing hub assembly in the top of the container;
      after the step of inserting the wall blade members and the sleeve members but before the step of inserting the paddle, inserting a retaining ring through the open bottom of the container so that the retaining ring receives the wall blade members; and
      after the step of inserting the paddle through the open bottom of the container, connecting a base assembly to close the bottom of the container.

16. A method as defined in claim 15, wherein:
   the step of inserting the wall blade members includes moving the wall blade members into engagement with the retaining baffle; and
   the step of inserting the paddle includes moving a shaft of the paddle through the retaining baffle and the centralizing hub assembly.

17. A method as defined in claim 16, wherein the step of assembling further includes applying grease over surfaces of the sleeve members, the wall blade members, the paddle shaft and the centralizing hub assembly.

* * * * *